United States Patent [19]

Seiler et al.

[11] 4,049,690

[45] Sept. 20, 1977

[54] METHOD OF PREPARING β-CHLOROETHYLTRICHLOROSILANE

[75] Inventors: Claus-Dieter Seiler, Rheinfelden; Hans-Joachim Vahlensieck, Wehr, both of Germany

[73] Assignee: Dynamit Nobel Aktiengesellschaft, Troisdorf, Germany

[21] Appl. No.: 636,880

[22] Filed: Dec. 2, 1975

[30] Foreign Application Priority Data

Dec. 24, 1974 Germany .............................. 2461480

[51] Int. Cl.$^2$ ............................ C07F 7/08; C07F 7/12
[52] U.S. Cl. ............................................... 260/448.2 E
[58] Field of Search .................................. 260/448.2 E

[56] References Cited

U.S. PATENT DOCUMENTS

| 3,801,614 | 2/1974 | Lohmann et al. | 260/448.2 E |
| 3,933,881 | 1/1976 | Fory et al. | 260/448.2 E |

OTHER PUBLICATIONS

Noll, "Chemistry and Technology of Silicones," Academic Press, N.Y. (1968), pp. 152 & 153.

*Primary Examiner*—Paul F. Shaver
*Attorney, Agent, or Firm*—Burgess, Dinklage & Sprung

[57] ABSTRACT

An improved process for the hydrochlorination of vinyltrichlorosilane to prepare β-chloroethyltrichlorosilane, which hydrochlorination is carried out by reacting the vinyltrichlorosilane with HCl in the presence of a Lewis catalyst, the improvement lying in carrying out the reaction at a temperature between 30° and 65° C, preferably at normal pressure.

6 Claims, No Drawings

METHOD OF PREPARING β-CHLOROETHYLTRICHLOROSILANE

BACKGROUND OF THE INVENTION

FIELD OF THE INVENTION

This invention relates to the hydrochlorination of vinyltrichlorosilane in the presence of a catalyst. More particularly, this invention relates to the virtually quantitative preparation of β-chloroethyltrichlorosilane by hydrochlorination of vinyltrichlorosilane in the presence of a Lewis catalyst at 30° to 65° C at about normal pressure.

It is known that β-chloroethyltrichlorosilane forms in the reaction of vinyltrichlorosilane with hydrochloric acid. Even when Lewis acids are used as catalysts, an equilibrium is established at reaction temperatures between 120° and 150° C, and accordingly nothing but low yields of chloroethyltrichlorosilane are obtained. The maximum yields amount to about 47 percent. In addition, appreciable amounts of silicon tetrachloride and α-chlorovinyltrichlorosilane are formed (Ind. & Eng. Chem. 45 (1953), pp. 367-374).

Attempts have been made to shift this equilibrium reaction more towards the β-chloroethyltrichlorosilane by performing this reaction between 0° C and 60° C with the application of pressure. On the basis of Le Chatelier's principle it has thus been possible to increase the yield to a maximum of 95 percent. See German Offenlegungsschrift No. 2,242,773.

Accordingly, it has become desirable to provide a process which will yield higher quantities of chloroethyltrichlorosilane than the 47 percent obtained according to prior art processes. More particularly, it has become desirable to provide a process for the preparation of β-chloroethyltrichlorosilane by a simple process wherein the β-chloroethyltrichlorosilane is obtainable in virtually quantitative yields. More especially, it has become desirable to provide such a process using readily available reactants such as vinyltrichlorosilane and hydrochloric acid.

SUMMARY OF THE INVENTION

In accordance with this invention an improved process for the preparation of β-chloroethyltrichlorosilane by reaction of vinyltrichlorosilane with hydrochloric acid in the presence of a Lewis acid catalyst is provided. The present process involves carrying out the reaction of vinyltrichlorisilane and hydrochloric acid at an elevated temperature within the range of 30° to 65° C at about normal pressure. Preferably, the catalyst employed has a concentration of 1.0 to 15 percent by weight based upon the weight of the vinyltrichlorosilane charged.

Suprisingly, it has been found that by carrying out the reaction at 30° to 65° C and at about normal pressure, virtually quantitative yields of β-chloroethyltrichlorosilane are obtained.

This result is suprising because according to Le Chatelier's principle one would have expected that, if a gas (HCL) reacts with a low-boiling compound ($CH_2$_$CH-Si-Cl_3$) at normal pressure, the yields would be lower than they are when pressure is applied.

In the reaction of the invention, virtually no by-products are produced if it is performed in the temperature range between 30° and 45° C. At a catalyst concentration higher than 2.5percent, the reaction is complete. At higher temperatures only $SiCl_4$ develops as a by-product, in amounts of less than 2 wt.-%. This $SiCl_4$ can easily be separated by distillation from the desired chloroethyltrichlorosilane.

The term "normal pressure" as used herein refers to the prevailing atmospheric pressure, differences of about 5percent above or below atmospheric being quite acceptable. Therefore, the normal pressure can be, say, between 740 and 790 mm Hg according to prevailing atmospheric conditions.

As catalysts, Lewis acids are used which have also been used in the procedures known heretofore. These include the chlorides of aluminum, iron, phosphorus, antimony, zinc and tin, the bromides of aluminum, iron and phosphorus, and boron trifluoride. Preferred catalysts are aluminum chloride and iron (III) chloride.

When the catalyst is used in amounts above 10percent, the formation of $SiCl_4$ takes place increasingly, especially at temperatures above 50° C. The preferred catalyst concentration is between 2.0 and 6.0 wt.-% with respect to the vinyltrichlorosilane charged.

β-chloroethyltrichlorosilane is a commercially important intermediate from which other products can be made which find application in agrarian chemistry and as adhesivizing agents.

β-chloroethyltrichlorosilane can be converted to a valuable agrarian chemical by a process which involves esterification of Cl-atoms bonded to the silicon atom with alkanols. The obtained silane-ester influences the growth of certain plants. (cf U.S. Pat. No. 3,998,257). These lower esters can also be transesterified with cellosolve to obtain silane-esters of the formula Cl—CH$_2$_CH$_2$_Si (O—CH$_2$_CH$_2$_O—R) (R= methyl, ethyl) which are applied in agriculture, too.

When it is converted into an adhesivizing agent, it is treated according to the following procedure: esterification to the above cited cellosolve-ester, which are further treated with $NH_3$ or ethylene-diamine to obtain NH$_2$_CH$_2$_CH$_2$_NH—CH$_2$_CH$_2$_Si (O—CH$_2$_CH$_2$_OR)$_3$ or H$_2$N—CH$_2$_CH$_2$_Si (O—CH$_2$_CH$_2$_O R)$_3$ (R= ethyl, methyl)

In order to more fully illustrate the invention and the manner of practicing the same, the following examples are presented.

EXAMPLES

EXAMPLE 1 (for comparison)

A jacketed glass four-necked flask having a 2-liter capacity and provided with stirrer, reflux condensor, thermometer and gas introduction tube was filled with 830 g (5.1 moles) of vinyltrichlorosilane and 20 g of anhydrous $AlCl_3$. Hydrogen chloride was introduced through the gas introduction tube and the temperature was maintained at 20° C by means of a thermostat. After a period of 3 hours a total of 200 g (5.5 moles) of HCl had been introduced. The experiment was interrupted and the reaction liquid was analyzed by gas chromatography. Only three weight-percent of the vinyltrichlorosilane had reacted to form β-chloroethyltrichlorosilane.

EXAMPLES 2 and 3

In the same apparatus as in Example 1 the same amounts of vinyltrichlorosilane and hydrogen chloride were reacted as in Example 1, with the use, of 20 g of $AlCl_3$. The performance of the experiment was the same as in Example 1, except that the temperature was maintained constant at 40° C in one case and 60° C in another. The results are shown in the following table.

|  | Example 2 | Example 3 |
|---|---|---|
| Reaction temperature (° C) | 40 | 60 |
| Reaction time (h) | 2 | 2 |
| β-Chloroethyltrichlorosilane content in the end product | 100 | 98.7 |

EXAMPLES 4–9

The amounts of vinyltrichlorosilane specified in Example 1 were reacted with hydrogen in the same manner as also specified therein, only the reaction temperature and the amount of catalyst being varied. The results are summarized in the following table.

|  | Example | | | | | |
|---|---|---|---|---|---|---|
|  | 4 | 5 | 6 | 7 | 8 | 9 |
| $AlCl_3$ content (wt.-%) | 1.5 | 1.5 | 5.0 | 5.0 | 10.0 | 10.0 |
| Reaction time (h) | 2.0 | 2.0 | 2.0 | 2.0 | 2.0 | 2.0 |
| Reaction temp. ° C | 40 | 60 | 40 | 60 | 40 | 60 |
| End product analysis: | | | | | | |
| a) $ClCH_2-CH_2-SiCl_3$ (wt.-%) | 88.8 | 99.7 | 100 | 98.3 | 99.9 | 98.2 |
| b) $SiCl_4$ (wt.-%) | — | 0.3 | — | 1.7 | 0.1 | 1.7 |
| c) $CH=CH-Si-Cl_3$ (wt.-%) | 11.2 | — | — | — | — | — |

What is claimed is:

1. In a process for the hydrochlorination of vinyltrichlorosilane with HCl to prepare β-chloroethyltrichlorosilane wherein the reaction is carried out in the presence of a Lewis acid catalyst at an elevated temperature, the improvement which comprises carrying out the process at a temperature between 30° and 65° C, at a pressure of 740–790 mm Hg while employing a concentration of catalyst in the range of 1.0 to 15% by weight, based upon the amount of vinyltrichlorosilane charged.

2. A process according to claim 1 wherein the process is conducted at a pressure of 740 to 790 mm Hg.

3. A process according to claim 1 wherein the Lewis acid catalyst is anhydrous aluminum trichloride.

4. A process according to claim 1 wherein the reaction is carried out at a temperature between 30° and 45° C.

5. A process according to claim 1 wherein the catalyst is present in a concentration higher than 2.5 % by weight, based upon the amount of vinyltrichlorosilane charged.

6. A process according to claim 1 wherein the Lewis acid catalyst is selected from the group consisting of an aluminum chloride, iron chloride, phosphorus chloride, antimony chloride, zinc chloride, tin chloride, aluminum bromide, iron bromide, phosphorus bromide, boron trifluoride and ammonium pentafluoride.

* * * * *

UNITED STATES PATENT AND TRADEMARK OFFICE
CERTIFICATE OF CORRECTION

PATENT NO. : 4,049,690
DATED : September 20, 1977
INVENTOR(S) : Claus-Dieter Seiler et al It is certified that error appears in the above-identified patent and that said Letters Patent are hereby corrected as shown below:

Title page, Ref. cited, change "Fory" to -- Föry --.

Col. 1, line 30, insert " " " " (quotation marks) around "Offenlegungsschrift".

Col. 1, line 67, change "2.5percent" to -- 2.5 percent --.

Col. 2, line 6, change "5percent" to -- 5 percent --.

Col. 2, line 16, change "10percent" to -- 10 percent --.

Col. 2, line 29, change "3,998,257" to -- 3,898,257 --.

Col. 2, line 49, change "condensor" to -- condenser --

Col. 2, line 64, change "the use," to -- the use again, --.

Signed and Sealed this

Ninth Day of May 1978

[SEAL]

Attest:

RUTH C. MASON
Attesting Officer

LUTRELLE F. PARKER
Acting Commissioner of Patents and Trademarks